(12) United States Patent
Smart et al.

(10) Patent No.: US 7,462,819 B2
(45) Date of Patent: Dec. 9, 2008

(54) STATISTICAL METHODS APPLIED TO SURFACE CHEMISTRY IN MINERALS FLOTATION

(75) Inventors: Roger St. C. Smart, Tennyson (AU); Mark Carl Biesinger, London (CA); Brian Robert Hart, London (CA)

(73) Assignee: The University of Western Ontario, London (CA)

( * ) Notice: Subject to any disclaimer, the term of this patent is extended or adjusted under 35 U.S.C. 154(b) by 420 days.

(21) Appl. No.: 11/434,261

(22) Filed: May 16, 2006

(65) Prior Publication Data

US 2006/0289740 A1 Dec. 28, 2006

Related U.S. Application Data

(60) Provisional application No. 60/681,135, filed on May 16, 2005.

(51) Int. Cl.
*G01N 31/08* (2006.01)
(52) U.S. Cl. .................. 250/282; 250/287; 702/32; 702/22
(58) Field of Classification Search .............. None
See application file for complete search history.

(56) References Cited

U.S. PATENT DOCUMENTS

| | | | | |
|---|---|---|---|---|
| 5,135,549 A * | 8/1992 | Phillips et al. | .................... | 95/8 |
| 5,175,430 A * | 12/1992 | Enke et al. | ................. | 250/282 |
| 7,072,773 B2 * | 7/2006 | Plumb et al. | .................. | 702/32 |
| 7,087,896 B2 * | 8/2006 | Becker et al. | ................ | 250/282 |
| 7,110,886 B2 * | 9/2006 | Ito et al. | ....................... | 702/22 |
| 7,418,352 B2 * | 8/2008 | Plumb et al. | .................. | 702/32 |

OTHER PUBLICATIONS

"Surface layers in base metal sulphide flotation", Minerals Engineering vol. 4, Issues 7-11 pp. 891-909, R. St. C. Smart Feb. 13, 2003.

"Diagnostic Surface Analysis in Sulfide Flotation", Smart et al, Ian Wark Research Institute, University of South Australia, 8 pages.

"Principal Component Analysis of TOF-SIMS Images of Organic Monolayers", Biesinger et al, Analytical Chemistry, vol. 74, No, =. 22, Nov. 15, 2002.

"An investigation of the CU (II) adsorption Mechanism on Pyrite by ARXPS and SIMS", Weisener et al, Mineral Engineering, vol. 13 No. 13 1329-1340, 2000.

(Continued)

*Primary Examiner*—David A. Vanore
(74) *Attorney, Agent, or Firm*—Lynn C. Schumacher; Hill & Schumacher

(57) ABSTRACT

The present invention provides a method of analysis which couples principle component analysis (PCA) with ToF-SIMS for obtaining surface chemical information from minerals. Statistical methods, based on the monolayer-sensitive time of flight secondary ion mass spectrometry (ToF-SIMS) technique, combined with principal component analysis (PCA) identifies combinations of factors strongly correlated (positively or negatively) in images or spectra from sets of data. In images, PCA selects these correlations from the mass spectra recorded at each of 256×256 pixels in a selected area of particles. In the image mode, PCA provides a much better method of selecting particles by mineral phase with clearer definition of particle boundaries due to multi-variable recognition.

12 Claims, 7 Drawing Sheets

OTHER PUBLICATIONS

"Surface Analytical Studies of Oxidation and Collector Adsorption in Sulfide Mineral Flotation" Smart et al, Topics Applied Phys 85, pp. 3-60, 2003.

"Principal component analysis applied to surface chemistry in minerals flotation" Biesinger et al, Met Soc, fifth UBC-McGill Biennial International Symposium, 73-86.

"Quantifying accidental activation. Part I. Cu ion production", Minerals Engineering 15, 2002, pp. 567-571, Lascelles and Finch.

"The activation of sulphide minerals for flotation: a review", Finkelstein, International Journal of Mineral Processing 52, 1997 81-120.

"The mechanism of copper activation of sphalerite" Gerson et al, Applied Surface Science 1999 207-223.

"Statistical Comparison of Surface Species in Flotation Concentrates and Tails from TOF-SIMS Evidence", Piantadosi et al, Minerals Engineering, vol. 13 No. 13, 1377-1394, 2000.

* cited by examiner

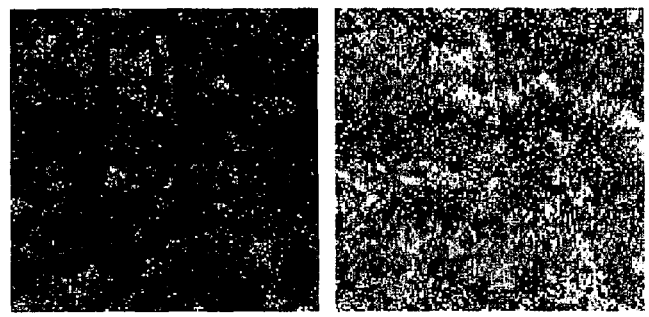
Figure 1
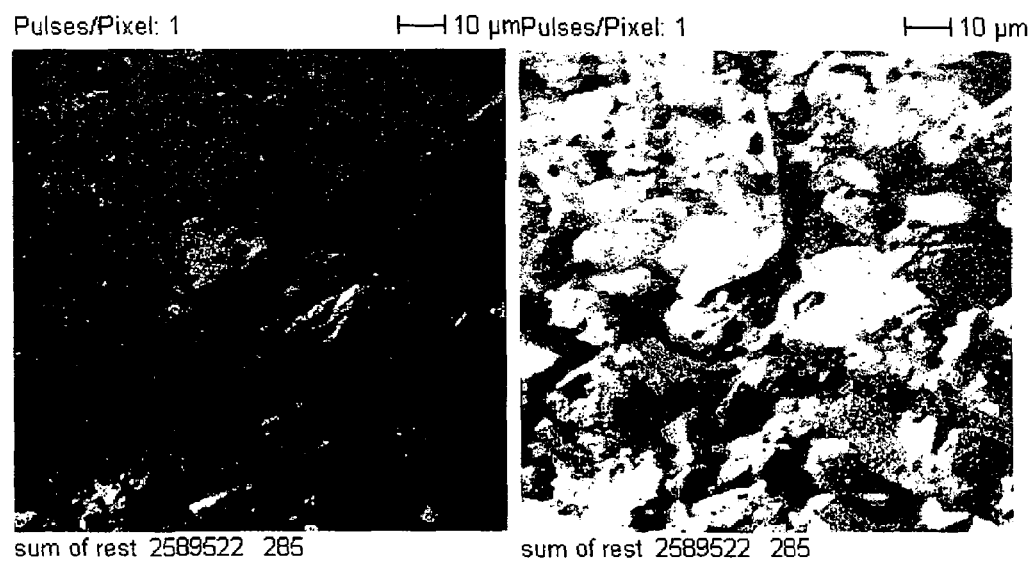
Figure 2
Figure 3

STATISTICAL METHODS APPLIED TO SURFACE CHEMISTRY IN MINERALS FLOTATION

CROSS REFERENCE TO RELATED U.S. APPLICATION

This patent application relates to, and claims the priority benefit from, U.S. Provisional Patent Application Ser. No. 60/681,135 filed on May 16, 2005, in English, entitled IMPROVED STATISTICAL METHODS APPLIED TO SURFACE CHEMISTRY IN MINERALS FLOTATION, and which is incorporated herein by reference in its entirety.

FIELD OF THE INVENTION

This invention relates to a method for analyzing surface chemistry of minerals for mineral phase recognition, and more particularly, the present invention uses principle component analysis applied to mineral samples analysed by time-of-flight secondary ion mass spectrometry (ToF-SIMS).

BACKGROUND OF THE INVENTION

In the selective separation of mineral phases by flotation, surface chemistry is the principal determinant of the average contact angle for a specific mineral phase in a flotation pulp. The average contact angle is, in turn, the principal determinant of the bubble-particle attachment efficiency ($E_a$) in the overall collection efficiency ($E_c$) from which the flotation rate constant can be determined (Ralston 1994). The recovery and selectivity in sulfide flotation is ultimately dependent on the relative rate constants of the different mineral phases. But the average contact angle is not only mineral-specific, based on a statistical average of the mineral particles in that phase, but also the contact angle for each particle is an average of hydrophobic and hydrophilic areas across the particle surface. Determination of this hydrophobic/hydrophilic balance by particle therefore requires selection of the particular mineral phase and statistical analysis of the particles with an estimation of the spread of values. In a flotation pulp containing many different mineral phases, different particle sizes of individual phases, adsorbed and precipitated species (often colloidal), and oxidised products, this is not a simple task.

The hydrophobic/hydrophilic balance by particle and its statistical average by mineral phase requires identification of the major species contributing to each category in surface layers (Smart 2003a). In addition to adsorbed collector molecules and their oxidised products (e.g. dimers), hydrophobicity can be imparted to sulfide mineral surfaces by oxidation to produce polysulfide $S_n^{2-}$ species resulting from loss of metal ions (usually $Fe^{2+}$) from surface layers. In acid solution, hydrophobic elemental sulfur can also be formed usually imaged in patches on the sulfide mineral surface (Smart et al. 2003b). Almost all other species found on sulfide mineral surfaces, such as oxide/oxyhydroxide/hydroxides, oxy-sulfur (e.g. sulfate), carbonate, hydrous silica and fine gangue particles, are essentially hydrophilic but may be in the form of localised particles, colloids and precipitates or continuous, reacted or precipitated surface layers (Smart et al. 2003b).

The action of collector molecules in inducing hydrophobicity can be assisted by activating species such as copper and lead ions that complex the collector on the surface. Previous research has shown that this activation can be inadvertently produced by dissolution and transfer via solution of these ions to mineral phases not intended to float (Smart 1991; Lascelles & Finch 2002; Finkelstein 1997). The mechanisms of activation of sphalerite (Gerson et al. 1999) and pyrite (Weisener & Gerson, 2000) by copper have been elucidated.

Hence, there is a need to find more reliable methods of mineral phase recognition in these complex surface chemistries and therefore, it would be very advantageous to provide a method which overcomes the aforementioned difficulties.

SUMMARY OF THE INVENTION

The method of the present invention couples principle component analysis (PCA) with ToF-SIMS for obtaining surface chemical information from minerals. This represents the first time that PCA has been applied to ToF-SIMS data representing surface chemical information from minerals. This method disclosed herein is particularly advantageous for application to diagnostic surface analysis and problem-solving in a wide range of mineral processing where surface chemical control is central to the efficacy of the process.

Several processes falling in this category include, but are not limited to: mineral separation by froth flotation, selective aggregation and electrostatic fields; metal release by leaching and solid/liquid transfer; aggregation of minerals in consolidation (including thickening), transfer or waste handling or disposal; and acid mine drainage control of waste rock and tailings. It also includes processes to react or coat minerals for improved durability and/or dispersion in aqueous or non-aqueous systems.

Broadly stated, the method is as follows. After appropriate sample preparation, the samples are analysed by time-of-flight secondary ion mass spectrometry (ToF-SIMS) in (raw data) imaging mode. That is, at each pixel of the ToF-SIMS image a corresponding mass spectrum is obtained. Once obtained this data is transferred to a suitable principal component analysis (PCA) software package capable of doing PCA on the obtained ToF-SIMS imaging dataset. PCA can be performed using a variety of data scaling techniques. The first principal component will generally represent the majority of topographic and matrix effects in the data and the subsequent principal components (now free of topographic and matrix effects) will represent the chemical constituents in the sample. From these principal components the mineral (or material phases) can now be ascertained. Returning to the original ToF-SIMS imaging data set region of interest (ROI) analysis of the specific mineral (or material) phases can now be undertaking. Comparisons between (the now clearly understood) phases can be completed and specific chemistries of each phase can be investigated.

Thus, the present invention provides a method of analysing mineral samples, comprising the steps of:

a) preparing a mineral sample for time-of-flight secondary ion mass spectrometry (ToF-SIMS);

b) analysing said prepared mineral sample by time-of-flight secondary ion mass spectrometry (ToF-SIMS) in an imaging mode to obtain a ToF-SIMS imaging data set in a region of interest, and corresponding mass spectrum at each pixel of the ToF-SIMS image;

c) performing a principle component analysis (PCA) on the obtained ToF-SIMS imaging data set in which the first principal component represents a substantial majority of topographic and matrix effects in the imaging dataset, and subsequent principal components represent chemical constituents in the sample;

d) determining from the subsequent principal components the mineral or material phases; and e) analysing specific mineral or material phases (regions of interest (ROI)) in the original ToF-SIMS imaging data set) and determining specific chemistries of each phase.

The method disclosed herein uses PCA applied to ToF-SIMS data in imaging mode for phase recognition of minerals or materials, thus representing the first time that PCA has been applied to ToF-SIMS data in imaging mode for phase recognition of minerals or materials. The present method overcomes the inherent difficulty of identification of the underlying, bulk phase from ToF-SIMS data normally produced from the first few molecular layers of the mineral or material.

The use of PCA processing of ToF-SIMS data described herein has produced a major advance in the ability of the operator to compare statistical information on surface species between regions of the same phase in samples from different processing procedures, streams or steps (including changes in reagents, time and/or temperature of reaction, physical agitation, solution conditions and processing units).

The combination of PCA with ToF-SIMS analysis has produced statistical separation of variables related to processing that were not revealed by previous analysis methods applied to the same data. The improved recognition of phase regions and statistical correlation of surface species by PCA has provided this advance as illustrated in the Examples disclosed herein.

The PCA selection of a sequence of principal components allows successive sets of correlated surface species to be examined providing more extensive information than the previous operator-selected sets of correlated factors.

The present invention is a method of using a high end Tof-SIMS Mass Spectrometer for measurement of surface chemistry of minerals and materials coupled with principal component analysis (PCA). The method provides refined analysis of mineral and material samples through improved phase selection and quantification of major and minor surface species. The novelty lies in how the time of flight mass spectrometer detects different surface species and how principal component analysis surpasses other processes in recognizing different phases and correlated surface species in samples.

This method is more efficient than the classic sequence of steps involved in performing minerals and materials analysis with a ToF-SIMS Mass Spec. The impurities are statistically detected through pattern recognition with greater accuracy and precision than in competitive methods.

A further understanding of the functional and advantageous aspects of the invention can be realized by reference to the following detailed description and drawings.

BRIEF DESCRIPTION OF THE DRAWINGS

The patent or application file contains at least one drawing executed in color. Copies of this patent or application publication with color drawing(s) will be provided by the Office upon request and payment of the necessary fee.

The invention will be more fully understood from the following detailed description thereof taken in connection with the accompanying drawings, which form a part of this application, and in which:

FIG. 1 is ToF-SIMS positive ion images of particles in the pyrite/sphalerite/chalcopyrite mixture, left: Zn ion distribution (raw), right: Zn ion distribution after normalization to the total ion image, Zn ROIs (regions of interest) representing a specific mineral phase appear bright in both images, images are 100×100 microns;

FIG. 2 is a schematic representation of the principles of principal component analysis used in the present invention;

FIG. 3 shows a ToF-SIMS total (positive) ion image of particles in the pyrite/sphalerite/chalcopyrite mixture. Left: linear scale. Right: log scale;

FIG. 4). Right: statistical analysis of Cu distribution between pyrite and sphalerite using the phase regions identified by PCA;

DETAILED DESCRIPTION OF THE INVENTION

ToF-SIMS Surface Analysis

Figure 4:
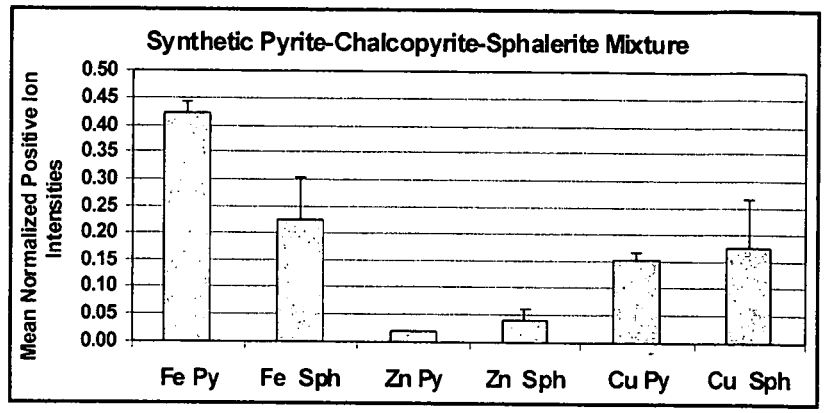
FIG. 4 shows statistical phase identification from single specie ion image identification and copper distribution between pyrite and sphalerite, line bars are 95% confidence intervals.

The ToF-SIMS technique, used in static mode, involves a very low flux of heavy ions (in this case, $Ga^+$) impacting surface layers with mass spectrometric analysis of the secondary ions emitted from the surface. In the time of routine measurement, only 1-2 surface atoms in 1000 are impacted. The secondary elemental and molecular fragment ions come from the first two molecular layers of the surface and provide a very detailed set of positive and negative mass fragments from simple ions, e.g. $Na^+$, $OH^-$ through to molecular ions of specific reagents, e.g. isobutyl xanthate $(CH_3)_2CHOCS_2^-$. Identification of molecular mass peaks for collectors, activators, depressants, precipitates and adsorbed species is possible with comparative surface concentrations by particle and by phase between feed, concentrate and tail streams. In the method developed at the Ian Wark Research Institute, a lateral distribution imaging of species by particle is combined with a statistical comparison of differences between streams by mineral phase (Piantadosi et al., 2000).

Single Specie Ion Image Mineral Phase Identification

Individual phase recognition in a multi mineral mixture was originally accomplished by scanning for regions of high ion yield peculiar to a selected mineral phase. Specific ion images were normalized to the total ion yield removing topographic and/or matrix effects in an attempt to clearly define the phase associated with the selected ion. FIG. 1 shows the ToF-SIMS positive ion images of particles in the pyrite/sphalerite/chalcopyrite mixture. Left: Zn ion distribution (raw). Right: Zn ion distribution after normalization to the total ion image. Zn ROIs representing a specific mineral phase appear bright in both images. Images are 100×100 microns. Regions of interest (ROI) were then mapped and mass spectra collected for 30 ROIs representing each mineral phase. Statistical analyses were performed on phase specific spectra after normalization to total ion yield and area.

Principal Component Analysis (PCA)

Consider a 256×256 pixel ToF-SIMS image data set obtained over a mass range of 1000 amu contains over $6.5 \times 10^7$ data points or variables. With such a large data set, extracting and analyzing the relevant data, in this case—mineral phases, becomes a major issue. Fortunately, the variables are usually correlated such that the most important information is contained in a smaller number of components. Principal component analysis is employed to determine these components.

Related to a ToF-SIMS imaging data matrix (X), each sample point (m), or pixel in the image, will have n variables (mass spectral intensities) associated with it. The data matrix X is organized into m rows and n columns. Calculation of the PCA model decomposes the data matrix X into submatrices represented in FIG. 2 and by the following equation:

$$X = t_1 p_1^T + t_2 p_2^T + \ldots t_k p_k^T \ldots t_q p_q^T \quad (1)$$

where $t_i$ are the scores (images), $p_i$ are the loadings (mass spectral intensities), $q \min\{m,n\}$, and the $t_1 p_1$ pairs are ordered by the amount of variance captured. The first principal component will account for as much of the variability in the data as possible, and each succeeding component will account for as much of the remaining variability as possible. In ToF-SIMS data, this first principal component is often associated with large topographic and matrix variations in the data (ion yield variations across the sample) (Biesinger et al., 2002). Successive components will describe the various chemical components in order of importance; in this case, mineral phases and other materials (gangue, mounting materials) within the imaged data set. These components will be relatively free of topographic and matrix effects.

FIG. 2 shows a schematic representation of the principles of principal component analysis. Generally the model is truncated, leaving some small amount of variance in a residual matrix (E) giving the following equation:

$$X = t_1 p_1^T + t_2 p_2^T + \ldots t_k p_k^T + E = T_k P_k^T + E \quad (2)$$

The PCA model is calculated using the following equations:

$$\text{cov}(X) = (X^T X)/(m-1) \quad (3)$$

$$\text{cov}(X) = \lambda_i p_i \quad (4)$$

where cov(X) is the covariance matrix of X, $X^T$ is the transpose of X and $\lambda_i$ are the eigenvalues. The amount of variance captured by $t_i p_i$ is proportional to $\lambda_i$. The resulting scores and loadings can then be examined and related to chemistry of the sample being explored. Typically, the majority of the variability within a system can be described in a relatively low number of principal components (scores and loading sets) allowing for an accelerated investigation of the data set. PCA is a well-established technique and a full description of it can be found elsewhere (Mardia et al., 1979, Massart et al., 1997).

PCA Software

PLS Toolbox 2.1 from Eigenvector Research Ltd. (Manson, Washington State, U.S.A.) running on Matlab 6.0 was the software used for PCA analysis. For each set of data as many significant mass peaks as possible were added to the peak list for analysis. Also included in the peak selection is the total remaining ion image (sum of ion intensity not selected as a specific peak) shown at mass zero in the loadings. Data was either "mean centred" or "autoscaled" prior to PCA. Mean centring is done by subtracting the column mean from each column, thus forming a matrix where each column has a mean of zero. For the "autoscaled" data, the data is first mean centred and each mean centred variable is then divided by its standard deviation resulting in variables with unit variance. This procedure puts all variables on an equal basis in the analysis. Thus, the less intense but more chemically significant higher mass peaks receive the same level of consideration in the analysis as the intense, low mass peaks. It should be noted that there are a variety of other software packages available that can also perform standard PCA analysis, for example Multi-Ion SIMS v 1.2 from BIOPHY Research (France).

The method comprises the steps of first preparing a mineral sample for time-of-flight secondary ion mass spectrometry (ToF-SIMS). The prepared mineral sample is then analysed by time-of-flight secondary ion mass spectrometry (ToF-SIMS) in an imaging mode to obtain a ToF-SIMS imaging dataset in a region of interest, and a corresponding mass spectrum at each pixel of the ToF-SIMS image. Then a principle component analysis (PCA) is performed on the obtained ToF-SIMS imaging dataset in which a first principal component represents a substantial majority of topographic and matrix effects in the imaging dataset, and subsequent principal components represent chemical constituents in the sample. The next step includes determining from the subsequent principal components the mineral or material phases, and then analysing specific mineral or material phases (regions of interest (ROI)) in the original ToF-SIMS imaging data set) and determining specific chemistries of each phase.

The analysis by time-of-flight secondary ion mass spectrometry (ToF-SIMS) is preferably carried out using a gallium ion primary beam or other appropriate ion source (In+, Au+, Bi+) suitable for imaging. An electron flood gun is generally also used to control sample charging. Analysis of a number of specific areas on the sample is carried out in order to obtain sufficient statistics for region of interest (ROI) analysis. The obtained data is mass calibrated and a peak list generated. Generally the peak list is made from any prominent peak in the spectra. Fifty to one hundred peaks or more are normally used. The image data is then converted to a binary format for use by the PCA software.

When performing a principle component analysis (PCA) on the obtained ToF-SIMS imaging data set, the method preferably includes loading the binary format data into a suitable PCA software program, extracting the image data and extracting the peak list data (which contains the masses selected). The data is then run through the PCA algorithm using the appropriate scaling procedures. Scaling generally includes mean-centering of the data or a combination of mean-centering and then dividing each mean-centered variable by its standard deviation (also known as "auto-scaling").

Determining the mineral or material phases from the subsequent principal components includes plotting out and examining the obtained scores and loadings from the principal component to determine the various mineral or material phases. This may require a number of iterations using both scaling methods.

When analysing specific mineral or material phases (regions of interest (ROI)) in the original ToF-SIMS imaging data set) and determining specific chemistries of each phase, the method includes identifying the specific areas in the original ToF-SIMS image dataset that correspond to specific mineral or material phases. The mass spectral data from these specific areas (regions of interest (ROI)) can then be normalized to the total ion yields in those specific areas. This data is now ready for comparison to other mineral phases or for analysis for specific chemical constituents.

The method of the present invention will now be illustrated using the following non-limiting example.

EXAMPLE 1

Sample Preparation and Mounting

The chalcopyrite/pyrite/sphalerite mixed mineral sample was conditioned with a pH 9 solution of sodium hydroxide for 20 minutes. Slurry samples were pressed into indium foil and transferred to the introduction chamber of the ToF-SIMS with the mineral surfaces still wet, i.e. without contact with air. The remaining liquid is then pumped away in the vacuum.

Results and Discussion

Mixed Mineral System

ToF-SIMS statistical analysis is reported for a chalcopyrite/pyrite/sphalerite mineral mixture conditioned at pH 9 for 20 minutes in order to study transfer of Cu from chalcopyrite via solution to the other two mineral surfaces. This mechanism can be responsible for their inadvertent flotation in copper recovery. In particular, preferential adsorption of copper ions between pyrite and sphalerite was examined. The system provided an opportunity to compare the results from the single specie ion image mineral phase identification to the PCA differentiation method and, to test the reliability of the latter. FIG. 3 shows the ToF-SIMS total (positive) ion image of particles in the pyrite/sphalerite/chalcopyrite mixture. Left: linear scale, Right: log scale.

The difficulty of phase recognition can be appreciated from FIG. 3 where the range of particle sizes is illustrated. Initially, phase recognition of pyrite and sphalerite was based on single specie ion (i.e. Fe, Zn respectively) image mineral phase identification as outlined above. Results after mineral phase differentiation, ROI mass spectra collection and processing for Fe, Zn and Cu are given in FIG. 4, which shows the statistical phase identification from single specie ion image identification and copper distribution between pyrite and sphalerite. Line bars are 95% confidence intervals.

The data indicate that pyrite differentiation is accomplished by mapping the Fe distribution even with the presence of Fe (bulk and surface) in sphalerite. Differentiation of sphalerite based on Zn distribution however is complicated by Zn on pyrite which results in some uncertainty as to species recognition. The Cu analyses by phase also suggests that there is no statistical difference between the copper adsorbed on pyrite and sphalerite, contrary to most studies which indicate a preference for adsorption on sphalerite but without direct evidence (Smart, 1991, Lascelles and Finch, 2002, Finkelstein, 1997). The lack of Cu selectivity is not related to mineral surface chemistry but to the poor differentiation between pyrite and sphalerite grains (see below).

Figure 5:
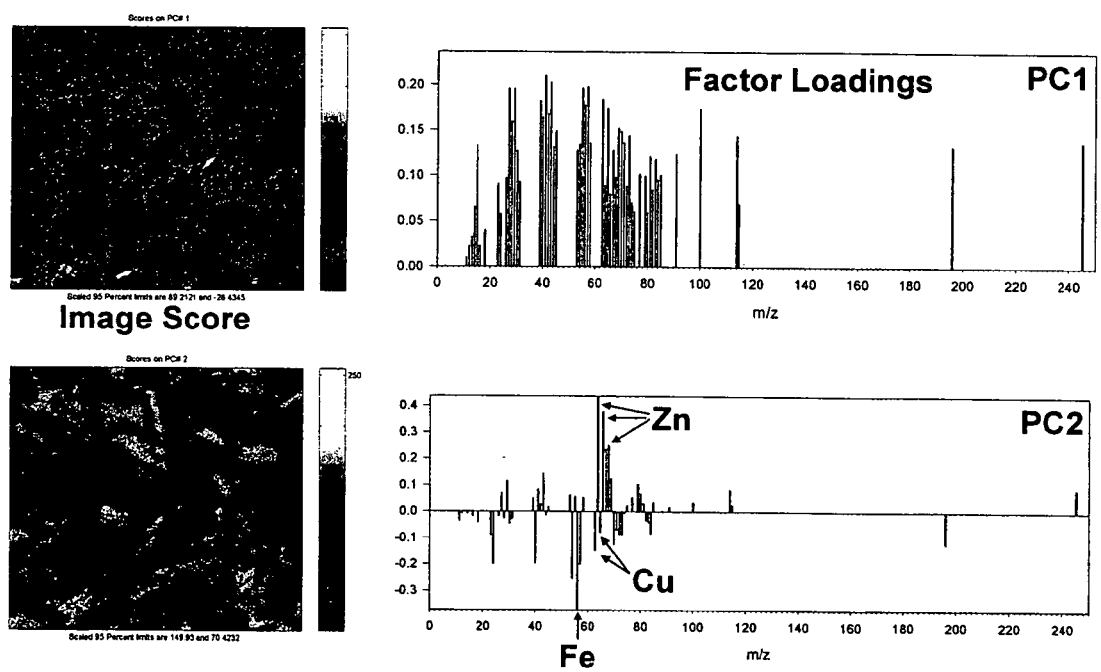
FIG. 5 shows principal component image scores and factor loadings for the chalcopyrite/pyrite/sphalerite mixture ("autoscaled" data, positive ion ToF-SIMS image data), images are 100×100 microns.

In an alternative statistical analysis, principal component analysis (PCA) was used to enhance phase recognition and definition of regions for mass spectral analysis. This is the first application of PCA to flotation surface chemistry. (Biesinger et al. 2004). In images, PCA selects correlations from the mass spectra recorded at each of 256×256 pixels ($6.5 \times 10^4$ data points) in a selected area of particles. FIG. 5 shows the image scores and factor loadings for the "autoscaled" positive ion image data set (four significant principal components). The first principal component, labelled PC1, shows factor loadings that are positive in weighting for all masses. This component is representative of the largest variance in the data set; topography and matrix (ion yield intensity) fluctuations. The second and subsequent PC's will then have this variance removed and as such are topography- and matrix-corrected.

PC2 shows positive weightings for zinc mass peaks and negative weighting for iron and copper mass peaks. Thus, bright areas on the image score are indicative of zinc rich (sphalerite) phases. The dark areas are thus rich in iron and copper; however, separation of pyrite and chalcopyrite phases is not yet accomplished.

Figure 6:
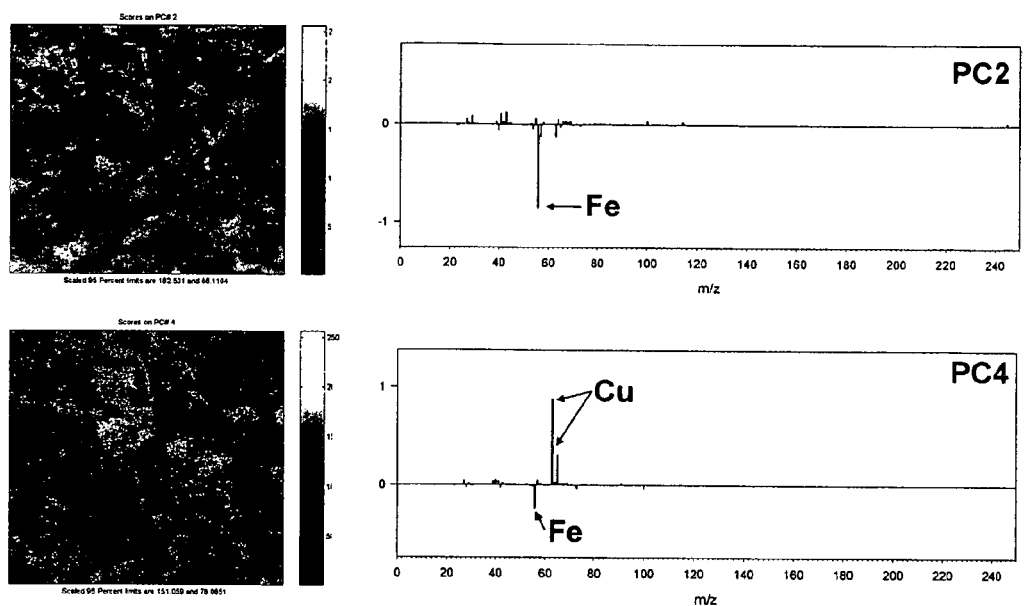
FIG. 6 shows principal component image scores and factor loadings (PC2 and PC4 only) for the chalcopyrite/pyrite/sphalerite mixture ("mean centered" data, positive ion ToF-SIMS image data), images are 100×100 microns.

As separation of pyrite and chalcopyrite had not been shown, a second PC analysis was carried out using "mean centred" data (FIG. 6). Using mean centred data will place more emphasis in the principal component analysis on stronger ion images (such as iron and copper). PC1 again produces factor loadings and images representative of the largest variance in the data set; topography and matrix (ion yield intensity) fluctuations and is usefully removed from subsequent PCs. PC2 in FIG. 6 shows a strong negative loading for iron and is similar in spatial distribution to the dark areas of PC2 from the "autoscaled" data set in FIG. 5. PC4 in FIG. 6 has strong positive loadings for copper. Thus the bright areas in the images are rich in copper giving positive chalcopyrite identification and by elimination, pyrite. Using these two PC analyses the chalcopyrite, pyrite, sphalerite, gangue materials and background (indium) components can be fully identified. It is therefore possible to select ROIs for each mineral with increased precision.

Figure 7:
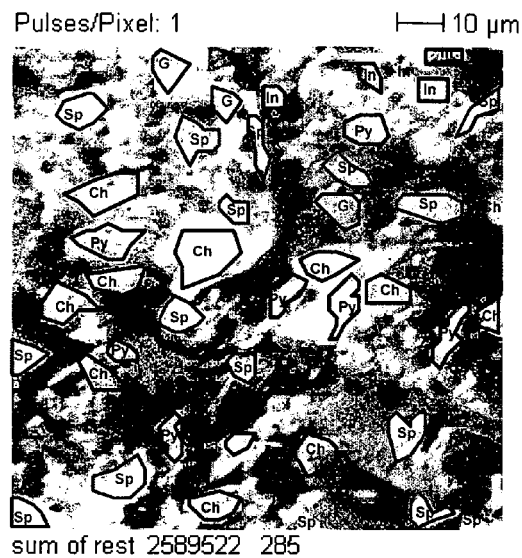
FIG. 7 shows PCA identification of mineral phases labelled: pyrite (Py); sphalerite (Sp); chalcopyrite (Ch); gangue materials (G), indium mounting material (In)

FIG. 5 shows the principal component image scores and factor loadings for the chalcopyrite/pyrite/sphalerite mixture ("autoscaled" data, positive ion ToF-SIMS image data). Images are 100×100 microns. FIG. 6 shows the principal component image scores and factor loadings (PC2 and PC4 only) for the chalcopyrite/pyrite/sphalerite mixture ("mean centered" data, positive ion ToF-SIMS image data). Images are 100×100 microns. FIG. 7 shows PCA identification of mineral phases labelled: pyrite (Py); sphalerite (Sp); chalcopyrite (Ch); gangue materials (G), indium mounting material (In).

Figure 8:
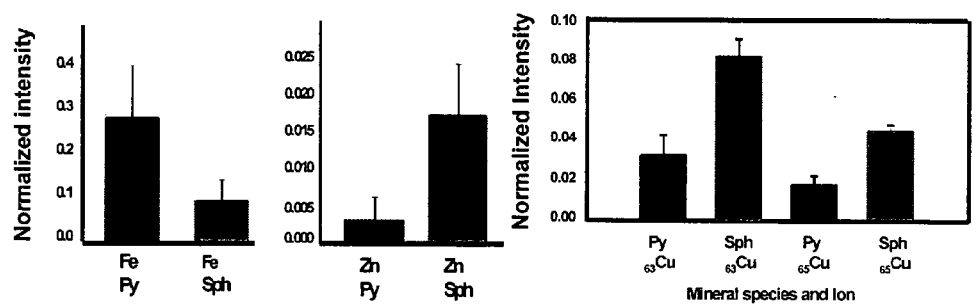
FIG. 8 shows PCA phase identification, pyrite from sphalerite. Left: note lower contributions from Zn on pyrite compared with Zn on sphalerite (c.f.

From the PC analysis, new ROI's were mapped (FIG. 7), spectra collected and the information processed in the same manner as the previous single specie ion image analyses. The differentiation of pyrite from sphalerite is clearly illustrated in the analyses of spectra collected from different ROIs (FIG. 8). The areas selected as pyrite contain appreciably more Fe than sphalerite; the Fe signal from sphalerite regions is consistent with a high-Fe sphalerite phase. Spectra for sphalerite grains are clearly Zn rich relative to pyrite; the Zn signal in the latter is likely superficial.

FIG. 8 shows PCA phase identification, pyrite from sphalerite. Left: note lower contributions from Zn on pyrite compared with Zn on sphalerite (c.f. FIG. 4). Right: statistical analysis of Cu distribution between pyrite and sphalerite using the phase regions identified by PCA. Importantly, using PCA phase identification, we now see a clear statistical separation of Cu distribution in favour of sphalerite (FIG. 8 left). The close agreement between the two copper isotopes provides confidence in the validity of the separation. This is also consistent with unwanted flotation of this phase in chalcopyrite circuits (Finkelstein, 1997). The transfer of copper ions from chalcopyrite dissolution to both pyrite (Smart, 1991) and sphalerite surfaces (Finkelstein, 1997) is confirmed by the surface analysis (FIG. 8 right). The new result is direct statistically-based evidence of preferential adsorption on sphalerite over pyrite in the same conditions and pulp solution.

EXAMPLE 2

The Inco Nickel-Copper Matte flotation process (Sproule et al., 1945, Tipman et al., 1976) separates chalcocite ($CU_2S$, Cc) from heazlewoodite (NiS, Hz) using a diphenylguanidine (DPG) collector and frother. The separation becomes less selective as the minerals move through the circuit. Possible reasons suggested for this loss include: inadvertent activation of Hz by dissolved copper ions; depression of Cc by dissolved nickel ions; lack of selectivity of the diphenylguanidine (DPG) collector including slow formation of Ni-DPG complexes at Hz surfaces and possible requirement of oxidation of Cc surfaces before effective DPG adsorption; depressant action of the calcium ions introduced as lime in the control of pH to 11-12 in this circuit. We have used the same PCA methods to study concentrate and tail samples from the operating plant.

Sample Preparation and Mounting

The chalcocite/heazlewoodite plant samples were collected from the Inco Matte Concentrator plant (C. Valenius) following the sampling methodology, developed and tested previously (Smart, 1991), to remove dissolved oxygen, snap-freeze to stop reaction. They were received in a frozen state, were thawed then washed 3 times in a pH 12 solution of sodium hydroxide. Each slurry sample was pressed into indium foil and transferred to the introduction chamber of the ToF-SIMS with the mineral surfaces still wet, i.e. without contact with air. The remaining liquid is then pumped away in the vacuum.

Results and Discussion: INCO Ni—Cu Matte Flotation Process

Figure 9A:
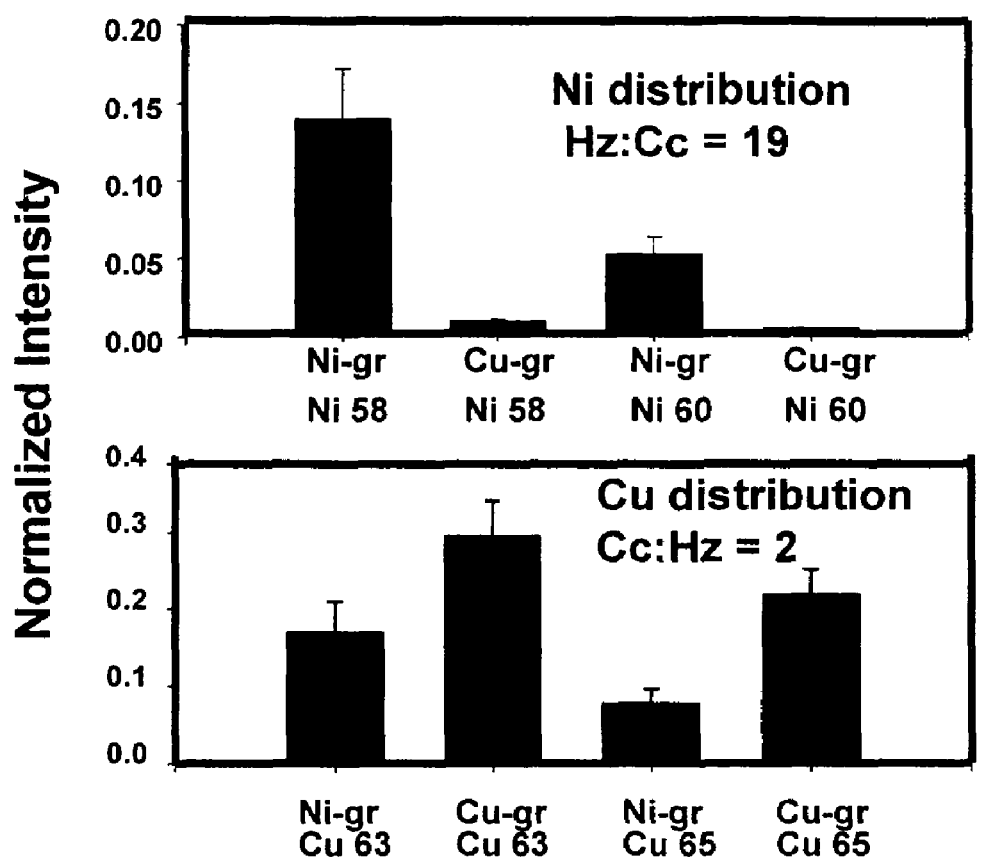
FIG. 9a shows a matte concentrator concentrate sample, PCA phase recognition with statistical analysis of phase regions for Ni and Cu transfer, upper: note the clear separation of surface nickel between Hz and Cc, lower: note the relatively high surface concentrations of Cu (both isotopes) on heazlewoodite (Ni-gr)
Figure 9B:
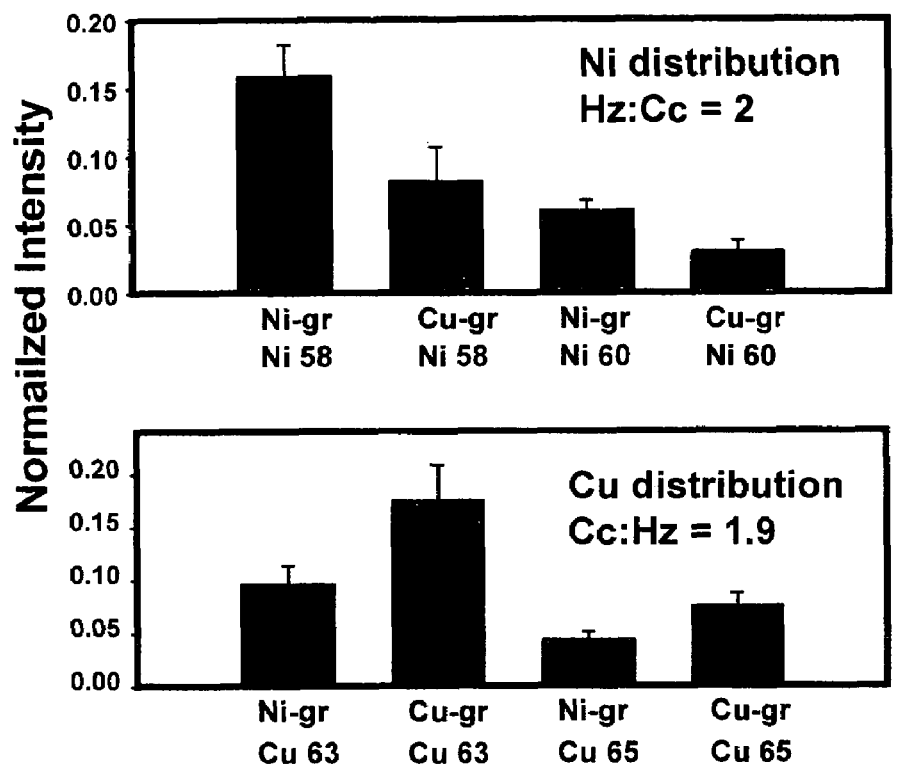
FIG. 9b shows a matte concentrator tails sample, PCA phase recognition with statistical analysis of phase regions for Ni and Cu transfer: Upper: note the loss of separation of surface nickel between Hz and Cc (c.f. concentrate), much higher surface concentrations on Cc in tails. Lower: note the still relatively high surface concentrations of Cu (both isotopes) on heazlewoodite (Ni-gr) in tails.

The principal components gave excellent recognition of the two mineral phases with reliable statistics on the regions selected. FIG. 9 illustrates some of the results from this study. Direct evidence of Cu transfer from chalcocite to heazlewoodite on particles inadvertently collected into the concentrate is shown in FIG. 9a shows evidence of Ni transfer from heazlewoodite to chalcocite in the tail samples is given in FIG. 9b. The correspondence in this and subsequent figures between the isotopes of Cu (63, 65) and Ni (58, 60) again gives some confidence in the correlations.

FIG. 9a shows a matte concentrator concentrate sample. PCA phase recognition with statistical analysis of phase regions for Ni and Cu transfer. Upper: note the clear separation of surface nickel between Hz and Cc. Lower: note the relatively high surface concentrations of Cu (both isotopes) on heazlewoodite (Ni-gr). FIG. 9b shows matte concentrator tails sample. PCA phase recognition with statistical analysis of phase regions for Ni and Cu transfer. Upper: note the loss of separation of surface nickel between Hz and Cc (c.f. concentrate). Much higher surface concentrations on Cc in tails. Lower: note the still relatively high surface concentrations of Cu (both isotopes) on heazlewoodite (Ni-gr) in tails.

The inadvertent flotation of Hz in the concentrate appears to be a result of Cu activation (0.16). There is also abundant Cu on Hz particles in the tails (0.08) but this is roughly half that in the concentrate. The Cu distribution between Cc and Hz particles in both concentrate and tails is the same within statistical 95% confidence intervals. The large statistical difference is in the Ni distribution where there is much (~5×) more hydrophilic Ni(II) ions on Cc particles in the tail compared with the concentrate. Hence, Cc in tails appears to be the result of high depressant hydrophilic loadings rather than absence of hydrophobic CuDPG surface species (see below). The exposure of Cu on Cc particles in the tails c.f. concentrate is ~0.5 corresponding to an increase in Ni exposure of ~7.5. Both Cu activation of Hz and Ni depression of Cc are clearly operating in this system.

Figure 10:
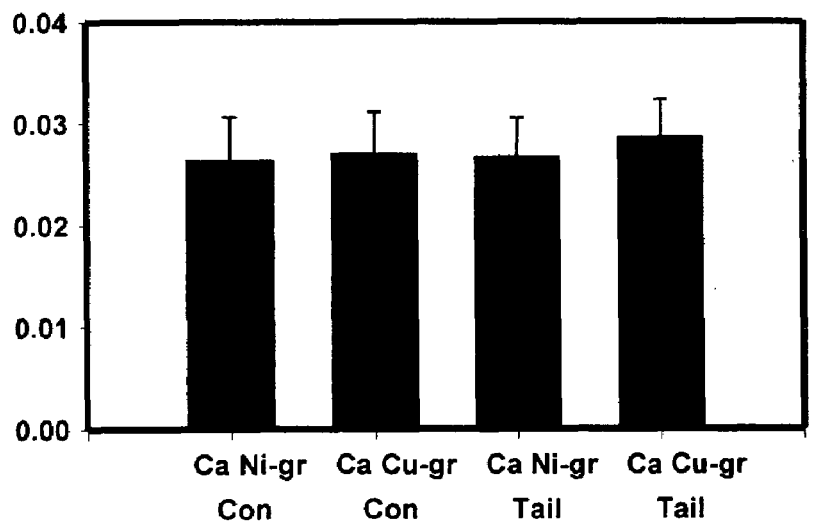
FIG. 10 shows matte concentrator PCA phase recognition with statistical analysis of phase regions for Ca signals in concentrate and tails samples.

The possible depressant action of Ca ions is not found to be selective. FIG. 10 shows matte concentrator PCA phase recognition with statistical analysis of phase regions for Ca signals in concentrate and tails samples. FIG. 10 shows that Ca is found on both Cc and Hz surfaces in concentrate and tails in statistically inseparable signals. Hence, Ca is adsorbed on all surfaces but is not discriminating between mineral particles of the same phase in concentrate and tails.

Figure 11:
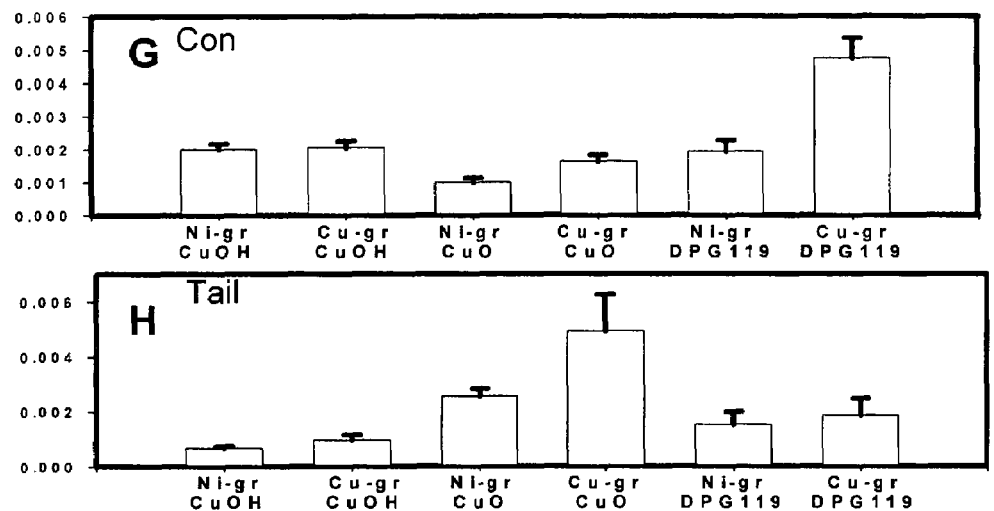
FIG. 11 shows comparison of CuOH, CuO and DPG mass signals; G: concentrate, high surface concentration of Cu-DPG complex on Hz (Ni-gr), H: Tail, no statistical difference in DPG between Cc (Cu-gr) and Hz (Ni-gr), higher CuOH on concentrate.

Mass signals for the Cu-DPG complex, represented in the mass 119 fragment, show higher (>1.8×) surface concentrations on Hz in the concentrate compared with the tail, FIG. 11, which shows a comparison of CuOH, CuO and DPG mass signals. G: Concentrate, high surface concentration of Cu-DPG complex on Hz (Ni-gr), H: Tail, no statistical difference in DPG between Cc (Cu-gr) and Hz (Ni-gr). Higher CuOH on concentrate. There is considerably more DPG (>4×) on Cc particles in concentrate than tails. In the tail samples there is no statistical difference in intensity of the DPG signals between Hz and Cc (FIG. 11). The reduced chalcocite hydrophobic/hydrophilic ratio is therefore related to the presence of Ni on the surface with a consequent reduction in bubble attachment efficiency.

There is also evidence that DPG may selectively attach to CuOH sites. There is considerably more (>2×) CuOH on both Cc and Hz particles in the concentrate than in the tails although more CuO is measured on both minerals in tails than concentrate. This finding is confirmed in Pearson product moment correlations by a high correlation coefficients between CuOH and DPG (119) on Hz in concentrate (0.70) and tails (0.90) and for Cc in concentrate (0.96). The correlation coefficient for Cc in tails is lower (0.3) presumably due to the high surface concentrations of Ni ions.

Figure 12:
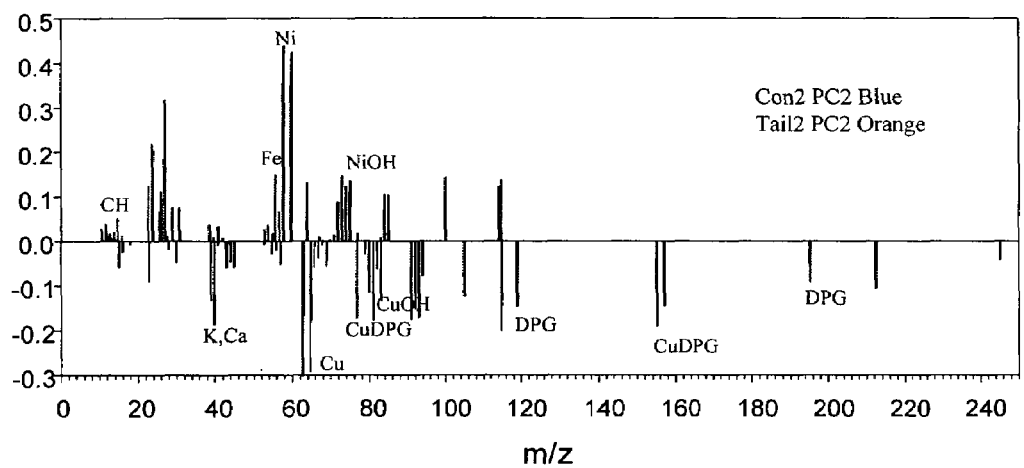
FIG. 12 shows an overlay of principal components (second) identifying Ni and Cu regions between concentrate and tails.

The most time-consuming steps in this analysis are the post-ToF-SIMS and PCA marking out of the ROIs, the collection of the mass spectra from the pixels in each ROI and the spread sheet statistical analysis of the collected spectra. The PCA analysis has already identified correlations of other species with major elements in particular mineral phases. FIG. 12 shows an overlay of principal components (second) identifying Ni and Cu regions between concentrate and tails. It may be possible to directly compare PCs identifying phases between concentrate and tails as in FIG. 12 but this analysis requires validation against the ROI method. If this is successfully validated, this methodology would allow full diagnostic assessment of surface speciation control in a single day turnaround.

FIG. 12 does confirm the high correlation of DPG with Cu in concentrate as CuDPG fragments and, conversely, no correlation of DPG with Ni and NiOH in concentrate or tail. These results agree with the ROI analysis. It also points to high correlation of Fe with Ni in concentrate which may be as a lattice substituent in Hz. The correlation of CuOH, K and Ca with tails in high Cu areas do not appear to agree with FIGS. 10 and 11 but the correlation of PC2 in the tails with Cu is weak (particularly for the 63 isotope) probably again due to substantial coverage by precipitated $Ni(OH)_2$.

SUMMARY OF EXAMPLES 1 AND 2

Diagnosis of the surface chemical factors playing a part in flotation separation of a valuable sulfide phase requires measurement of activating species that are statistically different between mineral phases. Time of flight secondary ion mass spectrometry (ToF-SIMS) has been used to identify sufficient particles of a specific mineral phase for reliable statistics determining a mean value for each species with 95% confidence intervals.

For a chalcopyrite/pyrite/sphalerite mineral mixture conditioned at pH 9 for 20 minutes, transfer of Cu from chalcopyrite occurred via solution to the other two mineral surfaces. Analysis based on Fe and Zn images indicated no statistical difference in the copper intensities on pyrite and sphalerite after this conditioning. Principal component analysis (PCA) is a better method of selecting mineral phases due to multi-variable recognition. The combination of auto-scaled and mean-centered principal components applied to this mineral mixture of pyrite, sphalerite and chalcopyrite, clearly separated the various mineral phases and enabled more reliable identification of statistical differences in copper intensities between the sphalerite and pyrite phases.

The method has been extended to samples from an operating flotation plant again with excellent phase recognition and diagnostic surface chemistry. Both copper and nickel ion transfer via solution have also been demonstrated in this study, the former relating to inadvertent activation of heazlewoodite and the latter to inadvertent depression of chalcocite. The methodology, with PCA phase recognition and statistical analysis, considerably extends the analytical basis of surface chemical control in flotation.

The present method represents the first time that PCA has been applied to ToF-SIMS data representing surface chemical information from minerals. This innovation allows application to diagnostic surface analysis and problem-solving in a wide range of mineral processing where surface chemical control is central to the efficacy of the process. Processes in this category include: mineral separation by froth flotation, selective aggregation and electrostatic fields; metal release by leaching and solid/liquid transfer; aggregation of minerals in consolidation (including thickening), transfer or waste handling or disposal; and acid mine drainage control of waste rock and tailings. It would also include processes to react or coat minerals for improved durability and/or dispersion in aqueous or non-aqueous systems.

The patented method represents the first time that PCA has been applied to ToF-SIMS data in imaging mode for phase recognition of minerals or materials. This innovation has overcome the inherent difficulty of identification of the underlying, bulk phase from ToF-SIMS data normally produced from the first few molecular layers of the mineral or material.

The use of PCA processing of ToF-SIMS data described herein has produced a major advance in the ability of the operator to compare statistical information on surface species between regions of the same phase in samples from different processing procedures (including changes in reagents, time and/or temperature of reaction, physical agitation, solution conditions and processing units) streams or steps.

The combination of PCA with ToF-SIMS analysis has produced statistical separation of variables related to processing that were not revealed by previous analysis methods applied to the same data. The improved recognition of phase regions and statistical correlation of surface species by PCA has provided this advance as illustrated in the Examples disclosed herein.

The PCA selection of a sequence of principal components allows successive sets of correlated surface species to be examined providing more extensive information than the previous operator-selected sets of correlated factors.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES

Biesinger M. C., Paepegaey P-Y., Mcintyre N. S., Harbottle R. R. and Petersen N. O., (2002), Principal Component Analysis of ToF-SIMS Images of Organic Monolayers, Analytical Chemistry, 74, 5711-5716.

Biesinger, M. C., Miller D., Francis J., Hart B. and Smart R. St. C., (2004), Principal Component Analysis Applied to Surface Chemistry in Minerals Flotation, in "Particle Size Enlargement in Mineral Processing". Proc. Fifth UBC-McGill Int. Conf. Fundamentals of Mineral Processing (Ed. J. S. Laskowski) Canadian Inst. Mining, Metallurgy and Petroleum ISBN 1-894475-52-6, pp. 73-88.

Gerson A. R., Lange A. G., Prince K. P. and Smart R. St. C., (1999), The Mechanism of Copper Activation of Sphalerite, Applied Surface Sci., 137, 207-223.

Finkelstein N. P., (1997), The Activation of Sulfide Minerals for Flotation: a Review, Int. J. Minerals Processing, 52, 81-120.

Lascelles D. and Finch J. A., (2002), Quantifying Accidental Activation I. Cu ion production, Minerals Engineering, 15, 567-571.

Mardia, K. V., Kent, J. T., and Bibby J. M., *Multivariate Analysis*, Academic Press, London, 1979, 213-254.

Massart, D. L., Vandeginste, B. G. M., Buydens, L. M. C., De Jong, S., Lewi, P. J., and Smeyers-Verbeke, J., *Handbook of Chemometrics and Qualimetrics: Part A*, Elsevier, Amsterdam, 1997, 519-556.

Piantadosi C., Jasieniak M., Skinner W. M. and Smart R. St. C., (2000), Statistical Comparison of Surface Species in Flotation Concentrates and Tails from ToF-SIMS Evidence, Minerals Engineering, 13, 1377-1394.

Ralston J., (1994), Bubble-Particle Capture, in *Flotation II* (Eds. S Castro and J. Alvarez) Publ. Andros Ltd. (Chile), Vol. 2, 1464.

Sproule K., Harcourt G. A. and Rose E. H., (1945), Froth Flotation of Nickel-Copper Matte, U.S. Pat. No. 2,432, 465.

Smart R. St. C, (1991), Surface Layers in Base Metal Sulphide Flotation., Minerals Engineering, 4, 891-909.

Smart, R. St. C., Jasieniak, M., Piantadosi C. and Skinner W. M., Diagnostic Surface Analysis in Sulfide Flotation, Proceedings Flotation and Flocculation: From Fundamentals to Applications, (Eds. J. Ralston, J D Miller and J Rubio) ISBN 0-9581414-0-1, 28 Jul.-2 Aug. 2002, Hawaii. Publ. Ian Wark Research Institute, University of South Australia, 241-248 (2003).

Smart R. St. C., Amarantidis J, Skinner W. M., Prestidge C. A., LaVanier L. and Grano S. G., (2003b), Surface Analytical Studies of Oxidation and Collector Adsorption in Sulfide Mineral Flotation in *"Solid-Liquid Interfaces"* (Eds K. Wandelt and S. Thurgate), Topics in Applied Physics, Springer-Verlag, Berlin, 85, 3-60.

Tipman N. R., Agar G. E. and Pare L., 1976, "Flotation Chemistry of the Inco Matte Separation Process", in Flotation, A. M. Gaudin Memorial Volume, (Ed. Fuerstenau M. C.), Amer. Inst. Min. Metall. Petrol. Eng. Inc., 1, Ch. 18, 528-548.

Weisener C. and Gerson A. R., (2000), Cu(II) Adsorption Mechanism on Pyrite: an XAFS and XPS Study, Surface and Interface Analysis, 30, 454-458.

Therefore what is claimed is:

1. A method of analysing mineral samples, comprising the steps of:
   a) preparing a mineral sample for time-of-flight secondary ion mass spectrometry (ToF-SIMS);
   b) analysing said prepared mineral sample by time-of-flight secondary ion mass spectrometry (ToF-SIMS) in an imaging mode to obtain a ToF-SIMS imaging data set in a region of interest, and corresponding mass spectrum at each pixel of the ToF-SIMS image;
   c) performing a principle component analysis (PCA) on the obtained ToF-SIMS imaging data set in which a first principal component represents a substantial majority of topographic and matrix effects in the imaging data set, and subsequent principal components represent chemical constituents in the sample;
   d) determining from the subsequent principal components the mineral or material phases; and
   e) analysing specific mineral or material phases (regions of interest (ROI)) in the original ToF-SIMS imaging data set) and determining specific chemistries of each phase.

2. The method according to claim 1 wherein step b) includes analysis by ToF-SIMS using a primary ion beam selected from the group consisting of Ga+, In+, Au+, Bi+ suitable for imaging.

3. The method according to claim 1 wherein step b) includes analysis of a number of specific areas on the sample carried out in order to obtain sufficient statistics for step e).

4. The method according to claim 1 wherein step b) the obtained data is mass calibrated and a peak list generated from any prominent peak in the spectra.

5. The method according to claim 1 wherein step b) includes converting the imaging data set to binary format data for use by principal component analysis software used to perform the PCA analysis.

6. The method according to claim 5 wherein step c) includes loading the binary format data into the principal component analysis software program, extracting the imaging data and extracting the peak list data containing the masses selected.

7. The method according to claim 5 wherein step c) includes processing the binary format data with the PCA algorithm using suitable scaling procedures.

8. The method according to claim 7 wherein the suitable scaling procedures includes mean-centering of the data or a combination of mean-centering and then dividing each mean-centered variable by its standard deviation.

9. The method according to claim 8 wherein step d) includes plotting out and examining the obtained scores and loadings from the principal component analysis to determine a presence of various mineral or material phases.

10. The method according to claim 9 wherein step e) includes identifying specific areas in the ToF-SIMS image data set that correspond to specific mineral or material phases.

11. The method according to claim 10 wherein mass spectral data from these specific areas regions of interest (ROI) are normalized to total ion yields in those specific areas.

12. The method according to claim 11 including comparing the normalized mass spectral data to other mineral phases or for analysis for specific chemical constituents.

* * * * *